United States Patent [19]
Bank et al.

[11] Patent Number: 5,616,760
[45] Date of Patent: Apr. 1, 1997

[54] PROCESS FOR REACTING ORGANODISILANES WITH ORGANIC HALIDES

[75] Inventors: Howard M. Bank, Freeland; Brian M. Naasz, DeWitt; Binh T. Nguyen, Midland, all of Mich.

[73] Assignee: Dow Corning Corporation, Midland, Mich.

[21] Appl. No.: 593,316

[22] Filed: Jan. 31, 1996

[51] Int. Cl.$^6$ .................................................. C07F 7/08
[52] U.S. Cl. .................................................. 556/468
[58] Field of Search .................................................. 556/468

[56] References Cited

U.S. PATENT DOCUMENTS

| | | | |
|---|---|---|---|
| 2,474,087 | 6/1949 | Barry et al. | 260/448.2 |
| 2,598,434 | 5/1952 | Mohler et al. | 556/468 |
| 2,598,435 | 5/1952 | Mohler et al. | 260/448.2 |
| 2,681,355 | 6/1954 | Barry et al. | 260/448.2 |
| 2,709,176 | 5/1955 | Bluestein | 556/468 |
| 2,787,627 | 4/1957 | Kuriyagawa et al. | 260/448.2 |
| 2,837,552 | 6/1958 | George et al. | 556/468 |
| 3,772,347 | 11/1973 | Atwell et al. | 260/448.2 E |
| 4,461,908 | 7/1984 | Takamizawa et al. | 556/468 X |
| 4,962,219 | 10/1990 | Halm et al. | 556/468 |
| 5,292,909 | 3/1994 | Chadwick et al. | 556/468 |
| 5,292,912 | 3/1994 | Chadwick et al. | 556/468 |
| 5,326,896 | 7/1994 | Chadwick et al. | 556/468 X |

*Primary Examiner*—Paul F. Shaver
*Attorney, Agent, or Firm*—William F. Boley

[57] ABSTRACT

A process for reacting organodisilanes with organic halides to form monosilanes. The process comprises heating a mixture comprising an organodisilane and an organic halide at a temperature within a range of about 100° C. to 350° C. The process is especially useful for reacting alkenyl chlorides, such as allyl chloride, with organodisilanes to form organomonosilanes having alkenyl substitution. The process is also useful for converting a high-boiling organodisilane containing fraction from a direct process for forming organosilanes into more useful monosilanes.

14 Claims, No Drawings

PROCESS FOR REACTING ORGANODISILANES WITH ORGANIC HALIDES

BACKGROUND OF INVENTION

The present invention is a process for reacting organodisilanes with organic halides to form monosilanes. The process comprises heating a mixture comprising an organodisilane and an organic halide at a temperature within a range of about 100° C. to 350° C. The process is especially useful for reacting alkenyl chlorides, such as allyl chloride, with organodisilanes to form monosilanes having alkenyl substitution. The process is also useful for converting a high-boiling organodisilane containing fraction from a direct process for forming organosilanes into more useful monosilanes.

The primary commercial method for producing organosilanes involves the reaction of an organic halide with elemental silicon. After the desired organosilanes have been recovered from the product mixture by distillation there remains a high-boiling residue which comprises among other components organodisilanes. Since these organodisilanes have very little commercial value it is desirable to convert them to the more useful monosilanes. The present invention relates to a process for converting organodisilanes to organomonosilanes by heating a mixture comprising an organodisilane and an organic halide at a temperature within a range of about 100° C. to 350° C. In the process the Si-Si bond of the organodisilane is broken resulting in the formation of two monosilanes, with the organic group of the organic halide substituting on one of the silicon atoms and the halogen group of the organic halide substituting on the other silicon atom.

Mohler et al., U.S. Pat. No. 2,598,435, describe a process where an organohalopolysilane containing a silicon-silicon linkage is heated at an elevated temperature to rupture the silicon-silicon bond and obtain a material of lower molecular weight.

Barry et al., U.S. Pat. No. 2,474,087, teach the reaction between an organic halide and a polyhalopolysilane such as hexachlorodisilane can be carried out at a temperature between 100° C. and 450° C. Barry et al. make no reference to organohalodisilanes.

Barry et al., U.S. Pat. No. 2,681,355, teach that when organohalodisilanes are cracked by the heat method of Mohler et al., supra, extensive coking of the reactor takes place. Barry et al., suggest this coking can be eliminated by the addition of hydrogen chloride to the process.

Numerous other methods have been reported where the heat cracking of organodisilanes is conducted in the presence of other compounds to facilitate the reaction and avoid the coking problem described by Barry et al., supra.

Kuriyagawa et al., U.S. Pat. No. 2,787,627, teach a method where a solution of trimethyltriethyldisilane was diluted in ethyl bromide and made to react upon the addition of dry bromine to the process along with refluxing.

Atwell et. al., U.S. Pat. No. 3,772,347, describe a process were organochlorodisilanes are reacted with an organic chloride in the presence of a transition metal complex comprising palladium and phosphorous.

Halm et al., U.S. Pat. No. 4,962,219, describe a process where an organohalodisilane is contacted with an organic halide in the presence of a metal, such as aluminum, which serves as a halogen acceptor, at a temperature greater than about 150° C.

The present inventors have unexpectedly discovered that a mixture comprising an organic halide and an organodisilane can be heated at a temperature within a range of about 100° C. to 350° C. to form monosilanes. In the present process coking does not occur and catalysts and other reactive compounds as described in the cited art are not required.

SUMMARY OF INVENTION

The present invention is a process for reacting organodisilanes with organic halides to form monosilanes. The process comprises heating a mixture comprising an organodisilane and an organic halide at a temperature within a range of about 100° C. to 350° C. The process is especially useful for reacting alkenyl chlorides, such as allyl chloride, with organodisilanes to form organomonosilanes having alkenyl substitution. The process is also useful for converting a high-boiling organodisilane containing fraction from a direct process for forming organosilanes into more useful monosilanes.

DESCRIPTION OF INVENTION

The present invention is a process for forming monosilanes from organodisilanes. The process comprises heating a mixture consisting essentially of an organodisilane described by formula $$R^1{}_n Si_2 X_{6-n}$$

and an organic halide described by formula $$R^2 X$$

at a temperature within a range of about 100° C. to 350° C., where each $R^1$ is an independently selected monovalent hydrocarbon radical comprising about one to 18 carbon atoms, $R^2$ is a monovalent hydrocarbon radical comprising about one to 18 carbon atoms, each X is independently selected from a group consisting of chlorine and bromine atoms, and n=1 to 6.

Heating of the mixture consisting essentially of the organodisilane and the organic halide can be effected in any standard pressurizable reactor suitable for contact with halosilanes. The process may be run as a batch, semi-continuous, or continuous process.

The mixture of the present process comprises organodisilanes described by formula $R^1{}_n Si_2 X_6$ where each $R^1$ is an independently selected monovalent hydrocarbon radical comprising about one to 18 carbon atoms and n=1 to 6. $R^1$ can be, for example, an alkyl such as methyl, ethyl, propyl, tert-butyl, and octadecyl; cycloalkyl such as cyclopentyl and cyclohexyl; alkenyl such as vinyl, allyl, and hexenyl; cycloalkenyl such as cyclopentenyl and cyclohexenyl; aryl such as phenyl, tolyl, and naphthyl; and aralkyl such as benzyl, beta-phenylethyl, and betaphenylpropyl. Preferred is when $R^1$ is methyl. The value n can be any value from one to six. It is preferred that n be a value within a range of four to six. Most preferred is when n is six. A preferred organodisilane for use in the present process is hexamethyldisilane. The present process can be used to convert a mixture of organodisilanes as described by the above formula into monosilanes.

The present process is useful for converting an organodisilane containing high-boiling fraction resulting from the reaction of an organic halide with elemental silicon to useful monosilanes. In a typical process for reacting an organic halide with elemental silicon, the process is conducted at a temperature of about 300° C. to 350° C. in the presence of suitable catalysts and gaseous product and feed along with fine particulates are continuously removed from the process. The removed materials are subsequently distilled to recover monosilanes, leaving a "high-boiling fraction." A preferred high-boiling fraction for use in the present process is one with a boiling point above about 70° C. resulting from the distillation of monosilanes from the reaction product of methyl chloride with elemental silicon. A typical Composition for such a high-boiling fraction comprises about 50–60 weight percent organodisilanes. The composition of a high-boiling fraction useful in the present process is described, for example, in Ferguson et al., U.S. Pat. No. 5,430,168, which is incorporated by reference for its teaching of such compositions. In some instances, it may be desirable to pre-treat the high-boiling fraction by a process such as filtration to remove particulates.

In addition to the organodisilanes, the mixture of the present process comprises an organic halide described by formula $R^2X$, where $R^2$ is a monovalent hydrocarbon radical comprising about one to 18 carbon atoms and each X is independently selected from a group consisting of bromine and chlorine atoms. Examples of useful structures for $R^2$ are the same as those described for $R^1$. It is preferred that the $R^2$ substituent of the organic halide be an alkenyl radical. It is preferred that X be chlorine. The preferred organic halide for use in the present process is allyl chloride.

The mole ratio of organic halide to organodisilane is not critical to the present process and can be varied from about 0.1:1 to 10:1. However, it is preferred that the mole ratio of organic halide to organodisilane be at least 1:1. Even more preferred is when the organic halide is present in the process in slight to moderate stoichiometric excess, that is within a range of greater than 1:1 to about 3:1.

The present process can be conducted at a temperature within a range of about 100° C. to 350° C. Preferred is when the process is conducted at a temperature within a range of about 150° C. to 250° C. The process does not require the presence of a catalyst at the described temperatures. The optimum temperature for conducting the present process will depend upon the organodisilane and organic halide added to the process. In general, the greater the number of organic substituents substituted on the silicon atoms of the organodisilane the lower an acceptable temperature can be. Likewise the greater the number of organic substituents substituted on the silicon atoms the faster the reaction occurs, with the time to complete conversion of the organodisilane to monosilanes varying from a few hours to several days.

The following examples are provided to illustrate the present invention. These examples are not intended to limit the scope of the claims herein.

The reactions reported in the examples were conducted in sealed pyrex glass tubes. A reaction mixture as described in each example was placed in the glass tube and cooled in a IPA/dry ice bath. The tube was then heat sealed and heated at the temperature and for the time described for each example. At the end of the described reaction period the content of the tube was cooled and analyzed by gas chromatography using a flame ionization detector (GC-FID). The results are reported as the area percent (area %) under the GC-FID trace. In the formulas of the examples Me is methyl.

EXAMPLE 1

The reaction mixture comprised 0.43 g (0.003 mol) of $Me_3SiSiMe_3$ and 0.33 g (0.004 mol) of allyl chloride. The mixture was heated at 150° C. for 54 hours, then cooled and analyzed by GC-FID. The analysis indicated the presence of no $Me_3SiSiMe_3$, 4.2 area % allyl chloride, 61.3 area % allylSiMe$_3$, and 31.9 area % $Me_3SiCl$.

EXAMPLE 2

The reaction mixture comprised 0.43 g of $Me_3SiSiMe_3$ and 0.33 g of allyl chloride. The mixture was heated at 200° C. for 6 hours, then cooled and analyzed by GC-FID. The analysis indicated the presence of no $Me_3SiSiMe_3$, 6.1 area % allyl chloride, 59.0 area % allylSiMe$_3$, and 31.6 area % $Me_3SiCl$.

EXAMPLE 3

The reaction mixture comprised 0.56 g (0.003 mol) of $Me_3SiSiMeCl_2$ and 0.3 g (0.004 mol) of allyl chloride. The mixture was heated at 200° C. for 26 hours, then cooled and analyzed by GC-FID. The analysis indicated the presence of 3.4 area % $Me_3SiSiMeCl_2$, 41.9 area % allyl chloride, 2.2 area % of allylSiMeCl$_2$, and 41.9 area % of $Me_3SiCl$.

EXAMPLE 4

The reaction mixture comprised 0.56 g (0.003 mol) of $ClMe_2SiSiMe_2Cl$ and 0.3 g (0.004 mol) of allyl chloride. The mixture was heated at 200° C. for 17 hours, then cooled and analyzed by GC-FID. The analysis indicated the presence of no $ClMe_2SiSiMe_2Cl$, no allyl chloride, 50.0 area % allylSiMeCl$_2$, and 28.4 area % of $Me_2SiCl_2$.

EXAMPLE 5

The reaction mixture comprised 0.68 g (0.003 mol) of $Cl_2MeSiSiMeCl_2$ and 0.3 g (0.004 mol) of allyl chloride. The mixture was heated at 200° C. for 17 hours, then cooled and analyzed by GC-FID. The analysis indicated the presence of 17.2 area % $Cl_2MeSiSiMeCl_2$, 20.2 area % allyl chloride, 31.9 area % allylSiMeCl$_2$, and 12 area % MeSiCl$_3$.

We claim:

1. A process for forming monosilanes from organodisilanes, the process comprising heating a mixture consisting essentially of an organodisilane described by formula $$R^1_n Si_2 X_{6-n}$$

and an organic halide described by formula $$R^2X$$

at a temperature within a range of about 100° C. to 350° C., where each $R^1$ is an independently selected monovalent hydrocarbon radical comprising about one to 18 carbon atoms, $R^2$ is a monovalent hydrocarbon radical comprising about one to 18 carbon atoms, each X is independently selected from a group consisting of chlorine and bromine atoms, and n=1 to 6.

2. A process according to claim 1, where $R^1$ is methyl.

3. A process according to claim 1, where n is a value within a range of four to six.

4. A process according to claim 1, where n is six.

5. A process according to claim 1, where the organodisilane is hexamethyldisilane.

6. A process according to claim 1 where the mixture comprises a high-boiling mixture resulting from distillation of the product of the reaction of methyl chloride and elemental silicon where the high-boiling mixture contains the organodisilane as a component thereof.

7. A process according to claim 1, where $R^2$ is an alkenyl radical.

8. A process according to claim 1, where X is chlorine.

9. A process according to claim 1, where the organic halide is allyl chloride.

10. A process according to claim 1, where the mole ratio of organic halide to organodisilane is within a range of about 0.1:1 to 10:1.

11. A process according to claim 1, where the mole ratio of organic halide to organodisilane is within a range of greater than 1:1 to about 3:1.

12. A process according to claim 1, where the temperature is within a range of about 150° C. to 250° C.

13. A process according to claim 1, where the organodisilane is hexamethyldisilane, the organic halide is allyl chloride, the mole ratio of organic halide to organodisilane is within a range of greater than 1:1 to about 3:1, and the temperature is within a range of about 150° C. to 250° C.

14. A process according to claim 1, where the mixture comprises a high-boiling mixture resulting from distillation of the product of the reaction of methyl chloride and elemental silicon where the high-boiling mixture contains the organodisilane as a component thereof, the organic halide is allyl chloride, the mole ratio of organic halide to organodisilane is within a range of greater than 1:1 to about 3:1, and the temperature is within a range of about 150° C. to 250° C.

* * * * *